(12) United States Patent
Park et al.

(10) Patent No.: US 11,534,544 B2
(45) Date of Patent: Dec. 27, 2022

(54) DEVICE FOR CONVEYING BIOLOGICAL MATERIAL

(71) Applicant: Daegu Gyeongbuk Institute of Science and Technology, Daegu (KR)

(72) Inventors: Suk Ho Park, Gwangju (KR); Hyun Chui Choi, Gwangju (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 506 days.

(21) Appl. No.: 16/734,906

(22) Filed: Jan. 6, 2020

(65) Prior Publication Data
US 2020/0297925 A1    Sep. 24, 2020

(30) Foreign Application Priority Data

Mar. 22, 2019  (KR) .................. 10-2019-0032876
May 14, 2019  (KR) .................. 10-2019-0056464

(51) Int. Cl.
*A61M 5/142* (2006.01)
*A61M 5/14* (2006.01)
*H01F 7/02* (2006.01)

(52) U.S. Cl.
CPC ...... *A61M 5/14276* (2013.01); *A61M 5/1409* (2013.01); *H01F 7/0247* (2013.01); *A61M 2205/0288* (2013.01); *A61M 2205/103* (2013.01); *A61M 2205/587* (2013.01)

(58) Field of Classification Search
CPC ............ A61M 5/14276; A61M 5/1409; A61M 2205/0288; A61M 2205/103; A61M 2205/587; A61M 5/31525; A61M 5/31526; A61M 5/31528; A61M 37/0069; A61M 2005/004; A61M 2005/005; H01F 7/0247; H01F 7/0242; A61B 1/041; A61B 5/6861; A61B 10/02; A61B 10/0266; A61B 10/0283; A61B 2010/0061; A61B 2017/00345; A61B 2034/303;
(Continued)

(56) References Cited

U.S. PATENT DOCUMENTS

2011/0166416 A1* 7/2011 Katayama .......... A61B 1/00082
                                                                    600/104
2019/0321555 A1* 10/2019 Biondi ................ A61M 5/3137

FOREIGN PATENT DOCUMENTS

| JP | 2005-124708 | 5/2005 |
|----|-------------|--------|
| JP | 10-2010-0052037 | 5/2010 |
| JP | 4734475 | 7/2011 |

(Continued)

OTHER PUBLICATIONS

KIPO, Office Action of KR 10-2019-0032876 dated Sep. 22, 2020.
KIPO, Office Action of KR 10-2019-0056464 dated Jul. 24, 2020.

*Primary Examiner* — Theodore J Stigell
*Assistant Examiner* — Phoebe Anne Staton
(74) *Attorney, Agent, or Firm* — Lex IP Meister, PLLC

(57) ABSTRACT

A device for conveying a biological material includes a body including an aperture configured to enable connection with an outside of the body and a chamber configured to store a biological material, a plurality of conveyors accommodated in the body and configured to convey the material, and a driver configured to select one of the plurality of conveyors, align the selected conveyor with the aperture, and move the selected conveyor to the outside of the body through the aperture.

7 Claims, 28 Drawing Sheets

(58) Field of Classification Search
CPC ... A61B 34/72; A61B 5/4839; A61B 1/00156; A61B 34/30
See application file for complete search history.

(56) References Cited

FOREIGN PATENT DOCUMENTS

| | | |
|---|---|---|
| JP | 5134972 | 1/2013 |
| KR | 10-2006-0030051 | 4/2006 |
| KR | 101003149 | 12/2010 |
| KR | 10-1620624 | 5/2016 |

* cited by examiner

DEVICE FOR CONVEYING BIOLOGICAL MATERIAL

CROSS-REFERENCE TO RELATED APPLICATION(S)

This application claims the priority benefit of Korean Patent Application No. 10-2019-0032876 filed on Mar. 22, 2019, and Korean Patent Application No. 10-2019-0056464 filed on May 14, 2019, in the Korean Intellectual Property Office, the disclosures of which are incorporated herein by reference for all purposes.

BACKGROUND

1. Field of the Invention

One or more example embodiments relate to a device for conveying a biological material.

2. Description of the Related Art

Devices for collecting and storing an intestinal biological material and for transferring a predetermined material to an intestinal portion are being developed. For example, an intestinal gas measuring capsule with a sensor for sensing hydrogen, oxygen, and carbon dioxide has been developed. The capsule may be helpful in checking a digestion rate according to an intestinal position and food intake of a user in real time. In another example, a capsule endoscope for biopsy a tissue at an intestinal lesion site as being controlled by an external magnetic field has been developed. In detail, ENDOSCOPE CAPSULE WITH BIOPSY TOOL is disclosed in KR Patent Publication No. 10-1620624.

SUMMARY

According to an aspect, there is provided a device for conveying a biological material, the device including a body including an aperture configured to enable connection with an outside of the body and a chamber configured to store a biological material, a plurality of conveyors accommodated in the body and configured to convey the material, and a driver configured to select one of the plurality of conveyors, align the selected conveyor with the aperture, and move the selected conveyor to the outside of the body through the aperture.

The driver may include a rotation driving element with a rotating shaft, and the plurality of conveyors may be rotated about the rotating shaft relative to the body by means of the rotation driving element.

The body may further include a plate, and the plate may include the aperture, define a portion of the chamber, and be rotated by means of the rotation driving element.

The rotation driving element may be configured to rotate the plate relative to the body by rotating the rotating shaft in a first direction.

The rotation driving element may be configured to rotate the body and the plate together by rotating the rotating shaft in a second direction, which is an opposite direction to the first direction.

The driver may further include a second plate on which the plurality of conveyors is arranged in a circumferential direction, and the second plate may be rotated by means of the rotation driving element.

The driver may be configured to move the body along a lumen of a target, and none of the plurality of conveyors may be aligned with the aperture while the body is moving.

The driver may include a linear driving element configured to move the selected conveyor toward the aperture or move the selected conveyor back from the aperture, and a linear guide configured to transfer power generated by the linear driving element to the selected conveyor, wherein the plurality of conveyors may each include a first magnetic element, and the linear guide may include a second magnetic element configured to magnetically coupled to the first magnetic element.

According to another aspect, there is provided a device for conveying a biological material, the device including a chamber, a channel inlet formed in the chamber and configured to allow an entry of a biological material, a channel outlet formed in the chamber on the same side as the channel inlet and configured to allow an exit of the biological material, a channel disposed in the chamber and configured to connect the channel inlet and the channel outlet, and a pump disposed on the channel and configured to pump the biological material from the channel inlet to the channel outlet.

The channel may contain a medium fluid configured to form a mixture with a set viscosity when mixed with the biological material.

the pump may be configured to discharge at least a portion of the medium fluid contained in the channel through the channel outlet toward a target having the biological material, and allow a mixed fluid, in which the discharged portion of the medium fluid is mixed with the biological material of the target, to enter the channel through the channel inlet.

The channel may include a first passage from the channel inlet to the pump, the first passage including a plurality of first bent portion, and a second passage from the pump to the channel outlet, the second passage including a plurality of second bent portion.

The pump may be disposed such that a flow volume of the second passage may be less than a flow volume of the first passage.

One of the plurality of first bent portion may be disposed adjacent to the channel inlet, and one of the plurality of second bent portion may be disposed adjacent to the channel outlet.

The channel and the pump may be configured to be detachable from the chamber.

The pump may include a driving element configured to operate in one of a first state in which connection of the channel is allowed and a second state in which connection of the channel is blocked or delayed, and a magnetic element configured to allow the driving element to operate when a magnetic field is applied thereto.

The driving element may operate in the first state when the magnetic field is applied to the magnetic element.

The magnetic element may have a magnetization direction which forms a set angle with respect to an axial direction of a drive shaft of the driving element.

The magnetic element may be configured to allow the driving element to operate when a rotating magnetic field or a reciprocating magnetic field is applied thereto.

The driving element may be configured to connect with the channel, guide a movement of the biological material, and maintain a pressure of the channel inlet to be lower than a pressure of the channel outlet.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
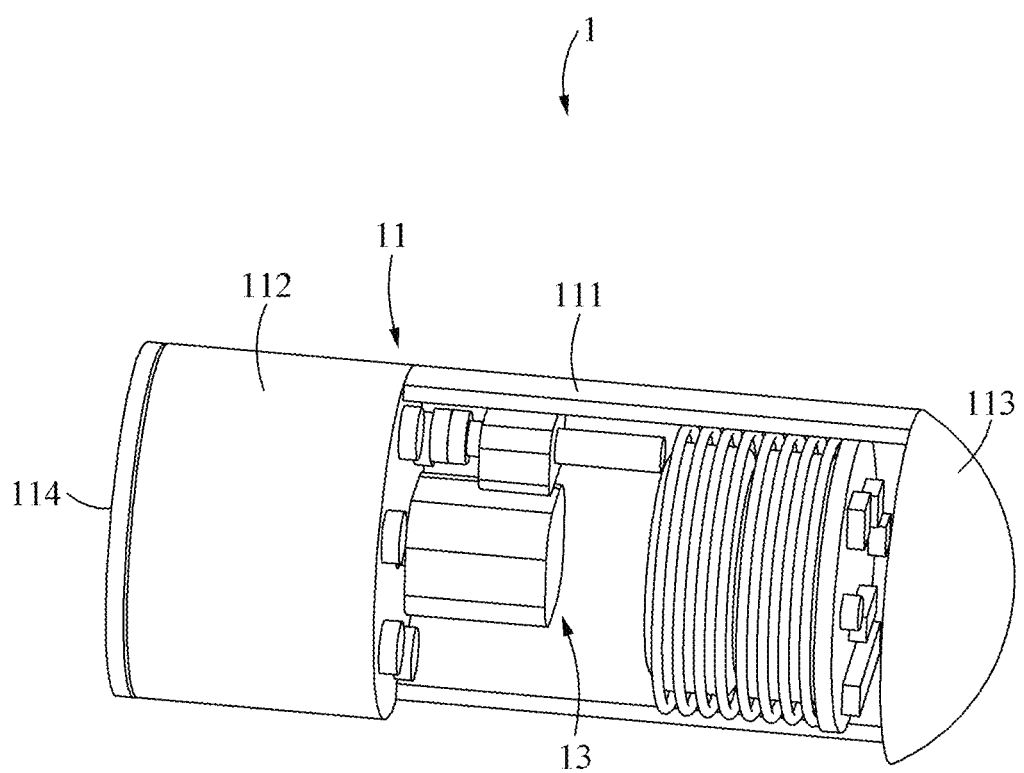
FIG. 1 is a perspective view illustrating a device for conveying a biological material according to an example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

As used in this application, the term "biological material" is used as the concept including microorganisms, drugs, and the like. Preferably, the biological material may include probiotic microorganisms.

As used in this application, the term "target" may include living things such as a human, an animal, and the like.

As used in this application, the term "lumen of a target" is used as the concept including an intestine of a living thing. For example, the lumen of the target may include a gastrointestinal tract, a small intestine, a large intestine, and the like of the living thing. Preferably, the lumen of the target may be a large intestine.

As used in this application, the term "conveying" is used as the concept including collecting, transporting, and transferring of a material.

Figure 2:
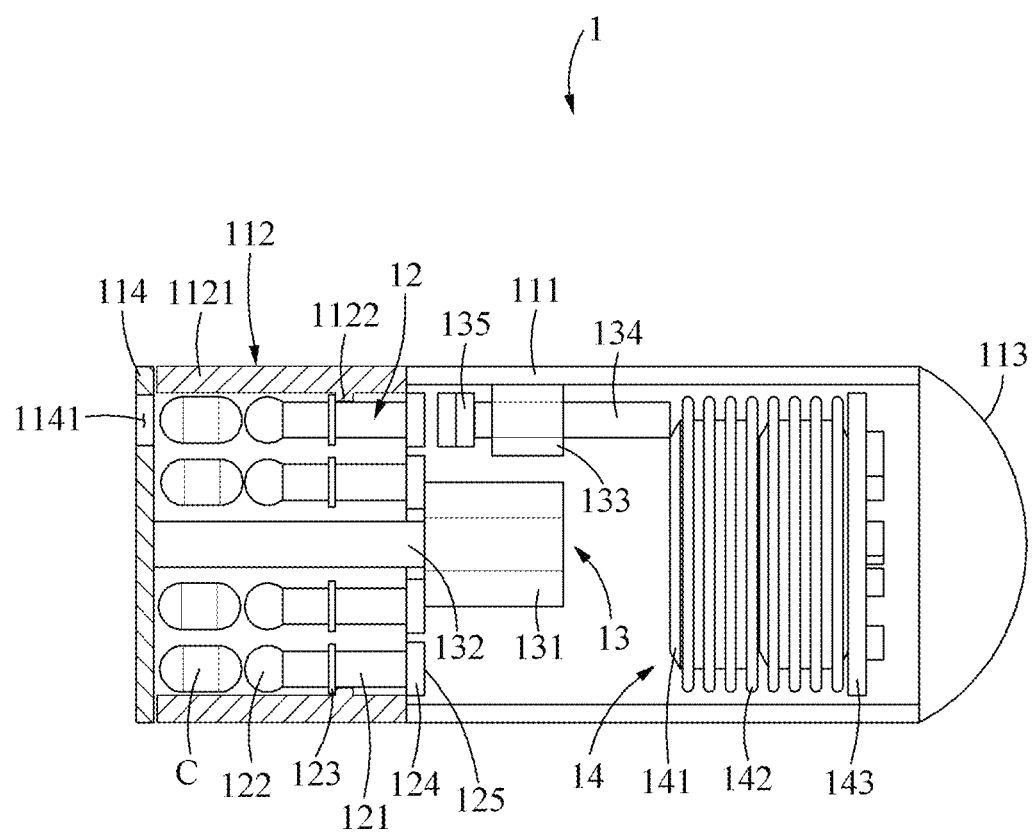
FIG. 2 is a cross-sectional view illustrating a device for conveying a biological material according to an example embodiment.

FIG. 1 is a perspective view illustrating a device for conveying a biological material according to an example embodiment, and FIG. 2 is a cross-sectional view illustrating the device for conveying a biological material according to an example embodiment.

Referring to FIGS. 1 and 2, a device 1 for conveying a biological material may move along a lumen of a target to store a set material at a desired site of the target and transfer the same, or to collect a biological material from a desired site of the target and store the same, or perform all the operations.

The device 1 for conveying a biological material may be provided in the shape of a capsule. This shape of the device 1 may help the target to easily accept oral administration of the device 1.

The device 1 for conveying a biological material may be provided in the size appropriate to move along the lumen of the target. In an example, the width of the device 1 may be about 0.3 mm to about 10 mm, preferably, about 1 mm to 8 mm. In an example, the length of the device 1 may be about 0.75 mm to about 25 mm, preferably, about 2 mm to about 20 mm.

The device 1 for conveying a biological material may include a body 11, a plurality of conveyors 12, a driver 13, and a circuit 14.

The body 11 may form the exterior of the device 1. The body 11 may protect internal elements of the device 1 when placed in the lumen of the target. For example, the body 11 may be provided in the shape of a capsule. The body 11 may include a first chamber 111, a second chamber 112, a tip portion 113, and a plate 114.

The first chamber 111 may include a cavity configured to accommodate at least a portion of the driver 13 and the circuit 14. The first chamber 111 may be provided in the shape of a hollow cylinder. However, the shape of the first chamber 111 is not limited thereto.

The second chamber 112 may accommodate the plurality of conveyors 12 and a remaining portion of the driver 13. Further, the second chamber 112 may accommodate a capsule C containing at least one biological material including a material to be transferred to a desired site of the target. Further, the second chamber 112 may store a biological material collected from a desired site of the target. The capsule C may be formed of a material appropriate to be dissolved in the lumen of the target. For example, the capsule C may be formed of a material which is not dissolved in a gastrointestinal tract so as to perfectly move to a large intestine of the target, but is dissolved in the large intestine. In this example, the capsule C may be coated with an enteric coating or a chitosan coating.

Figure 4:
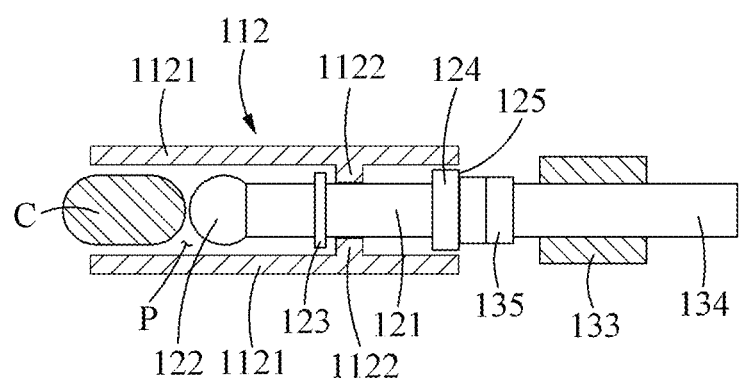

The second chamber 112 may include a plurality of sections configured to store a plurality of types of biological materials, and a plurality of partitions configured to physically separate the plurality of sections. In this example, different types of biological materials may be stored respectively in the plurality of sections. For example, the plurality of sections may be provided in the shape of a channel. The plurality of sections may be defined by an inner wall 1121 of the second chamber 112. Referring to FIG. 4, the plurality of sections may be implemented as a channel P defined by the inner wall 1121. Further, a stopper 1122 may be formed on the inner wall 1121 to restrict a movement of the conveyor 12, which will be described later.

The first chamber 111 and the second chamber 112 may be arranged in a row in a longitudinal direction of the body 11. For example, the first chamber 111 may be disposed in the front portion of the body 11, and the second chamber 112 may be disposed in the rear portion of the body 11. However, example embodiments are not limited thereto. In another example, the first chamber 111 may be disposed in the rear portion of the body 11, and the second chamber 112 may be disposed in the front portion of the body 11.

The tip portion 113 may form the front portion of the body 11. The tip portion 113 may be in the shape of a domelike, streamlined, curved surface. However, the shape of the tip portion 113 is not limited thereto. The tip portion 113 may be provided in the first chamber 111, as shown in FIGS. 1 and 2. However, when the second chamber 112 is disposed in the front portion of the body 11 as in the above example, the tip portion 113 may also be provided in the second chamber 112.

The plate 114 may form the rear portion of the body 11. Further, the plate 114 may protect a structure accommodated in the body 11 together with the first chamber 111 and the second chamber 112. The plate 114 may be provided in the shape of a disk. However, the shape of the plate 114 is not limited thereto. The plate 114 may be provided in the second chamber 112, as shown in FIGS. 1 and 2. However, when the first chamber 111 is disposed in the rear portion of the body 11 as in the above example, the plate 114 may also be provided in the first chamber 111.

The plate 114 may rotate. In an example, the plate 114 may rotate in a first direction together with the first chamber 111, the second chamber 112 and the tip portion 113. Meanwhile, the plate 114 may rotate in a second direction, which is an opposite direction to the first direction, relative to the first chamber 111, the second chamber 112 and the tip portion 113. Here, the first direction may be one of a clockwise direction and a counterclockwise direction when the tip portion 113 is viewed from the front, and the second direction may be the other of the clockwise direction and the counterclockwise direction. In another example, the plate 114 may rotate relative to the first chamber 111, the second chamber 112 and the tip portion 113 even when rotating either in the first direction or in the second direction.

The plate 114 may include an aperture 1141. In a preferable example, the plate 114 may include a single aperture 1141. The aperture 1141 may enable connection between an inside of the body 11 and an outside of the body 11. For example, the capsule C accommodated in the second chamber 112 may be transferred through the aperture 1141 to a desired site of the target, or a biological material may be collected through the aperture 1141 from a desired site of the target. The aperture 1141 may be provided mostly in the shape of a circle. However, the shape of the aperture 1141 is not limited thereto. The aperture 1141 may be formed in a portion apart from the center of the plate 114. However, example embodiments are not limited thereto. The aperture 1141 may be set in view of the size of the capsule C to be used, the typical size of a biological material to be collected, and the size of the conveyor 12 which will be described later.

The plate 114 may include an opening and closing element (not shown). The opening and closing element may be provided in the aperture 1141. The opening and closing element may selectively allow connection between the outside of the body 11 and an inside of the second chamber 112. For example, the opening and closing element may have a valve-shaped structure.

The first chamber 111, the second chamber 112, the tip portion 113, and the plate 114 may have substantially the same width. Here, the "width" refers to a maximum distance from one side of the element to the other side. For example, when the first chamber 111, the second chamber 112, the tip portion 113, and the plate 114 each have a circular cross section, the width thereof may be the diameter thereof.

The conveyor 12 may convey a material. For example, the material to be conveyed may be contained in the capsule C such that the material may be transferred from the inside of the second chamber 112 to the outside through the aperture 1141. In another example, the material to be conveyed may be a biological material collected from a desired site of the target.

The conveyor 12 may be provided in the substantially elongated shape. This shape may be appropriate to be accommodated in the second chamber 112 and convey a material through the aperture 1141. However, the shape of the conveyor 12 is not limited thereto. The conveyor 12 may be provided in any shape to achieve the purpose described above.

The conveyor 12 may be accommodated in the second chamber 112. However, unlike FIGS. 1 and 2, when the first chamber 111 is disposed in the rear portion of the body 11, the conveyor 12 may be accommodated in the first chamber 111.

The plurality of conveyors 12 may be arranged in a circumferential direction around a rotating shaft 132 which will be described later.

The conveyor 12 may include a rod 121, a conveying element 122, a first catch 123, and a second catch 124.

The rod 121 may move toward the aperture 1141 or move back from the aperture 1141 in the second chamber 112. The rod 121 may be provided in the elongated shape having a length. The rod 121 may be accommodated in the second chamber 112. The rod 121 may be provided in the shape extending from one end of the second chamber 112 toward the other end.

The conveying element 122 may transfer the capsule C accommodated in the second chamber 112 to the outside of the body 11 through the aperture 1141. In this example, when the rod 121 moves forward in the longitudinal direction thereof, the conveying element 122 may push the capsule C, and the pushed capsule C may be discharged through the aperture 1141 and transferred to a desired site of the target. The conveying element 122 may be provided at a rear end portion of the rod 121. The conveying element 122 may be provided in the three-dimensional shape mostly having a circular or elliptical cross section. The width of the conveying element 122 may be greater than the width of the rod 121, and may be substantially the same or less than the size of the aperture 1141.

The conveying element 122 may collect a biological material from a desired site of the target outside of the body 11. The conveying element 122 may include a sorbent configured to sorb the biological material. For example, the sorbent may include a sponge, and polystyrene of Dacron®.

The first catch 123 may be caught on a first side of the stopper 1122 formed on the inner wall 1121 of the second chamber 112. Meanwhile, the second catch 124 may be caught on a second side, which is an opposite side of the first side of the stopper 1122. The first catch 123 and the second catch 124 may protrude in a radial direction of the rod 121. The first catch 123 may be provided at the middle portion of the rod 121, and the second catch 124 may be provided at an end portion on the opposite side of the end portion of the rod 121 in which the conveying element 122 is provided. In the above structure, the distance between the first catch 123 and the second catch 124 may define the distance the rod 121 moves forward and backward in the longitudinal direction thereof.

The conveyor 12 may include a first magnetic element 125. The first magnetic element 125 may be provided in the second catch 124. The first magnetic element 125 may be magnetically coupled to a second magnetic element 135 which will be described later.

The driver 13 may drive the body 11 and the plurality of conveyors 12. The driver 13 may drive the body 11 such that the body 11 may move along the lumen of the target. Since the body 11 moves along the lumen of the target, the body 11 may transfer desired materials to various sites of the target, and collect various types of biological materials from various sites of the target. Further, the driver 13 controls rotations of the first chamber 111, the second chamber 112, the tip portion 113, and the plate 114. Further, the driver 13 may control movements of the plurality of conveyors 12.

The driver 13 may be disposed at a portion physically separate from the capsule C to be transferred to the outside of the body 11 or a biological material to be collected from the outside of the body 11 in the body 11. For example, when the capsule C or the biological material is disposed in the second chamber 112, at least a portion of the driver 13 may be disposed in the first chamber 111.

The driver 13 may include a rotation driving element 131, the rotating shaft 132, a linear driving element 133, a linear guide 134, and the second magnetic element 135.

The rotation driving element 131 may generate rotational power. For example, the rotation driving element 131 may include a rotary motor. The rotation driving element 131 may be disposed in the first chamber 111.

The rotating shaft 132 may transfer the rotational power to the plate 114. The rotating shaft 132 may be connected to the rotation driving element 131, and extend from the rotation driving element 131 toward the plate 114 to be connected to the plate 114. The rotating shaft 132 may be disposed in the second chamber 112. When the rotation driving element 131 operates, the rotating shaft 132 and the plate 114 may rotate together.

The linear driving element 133 may generate linear power. For example, the linear driving element 133 may include a linear motor. The linear driving element 133 may be disposed in the first chamber 111.

The linear guide 134 may move in a linear direction and transfer the linear power to the conveyor 12. The linear guide 134 may be connected to the linear driving element 133. The linear guide 134 may be disposed in the first chamber 111. When the linear driving element 133 operates, the linear guide 134 may move toward the conveyor 12 or move in a direction away from the conveyor 12.

The second magnetic element 135 may be magnetically coupled to the first magnetic element 125 of the conveyor 12. The second magnetic element 135 may be provided at an end portion of the linear guide 134. When the linear driving element 133 operates, the linear guide 134 may move in the linear direction, such that the second magnetic element 135 provided at the end portion of the linear guide 134 is coupled to the first magnetic element 125 of the conveyor 12, and the linear power of the linear guide 134 may be transferred to the conveyor 12.

Alternatively, the driver 13 may not include the second magnetic element 135. In this example, when the linear driving element 133 operate, the linear guide 134 may directly push the second catch 124, such that the conveyor 12 may move along the inner wall 1121 of the second chamber 112 toward the aperture 1141.

The circuit 14 may include an electric energy storing element 141, a communication element 142, and a control element 143. The electric energy storing element 141 may supply electric energy to the driver 13. For example, the electric energy storing element 141 may include a battery. The communication element 142 may communicate with a computer outside of the device 1. The communication element 142 may include a signal generator configured to generate an externally recognizable position signal. The position of the device 1 may be detected based on the position signal generated by the signal generator. For example, the communication element 142 may generate a radio frequency signal (RF signal). In another example, the communication element 142 may generate a magnetic field. The communication element 142 may be implemented by an antenna, a permanent magnet, or an electromagnet. The control element 143 may control the driver 13, the electric energy storing element 141, and the communication element 142. For example, the control element 143 may include a circuit board.

The device 1 for conveying a biological material may be detected by an external signal in the lumen of the target. In an example, the position of the device 1 in the lumen of the target may be detected by an external X-ray. In another example, the position of the device 1 in the lumen of the target may be detected by an external ultrasonic wave.

The position of the device 1 for conveying a biological material may be detected in real time in the manners described above. When the device 1 reaches a desired site of the target through appropriate position control, the device 1 may transfer a desired material to the site, or collect a biological material from the site.

Figure 3:
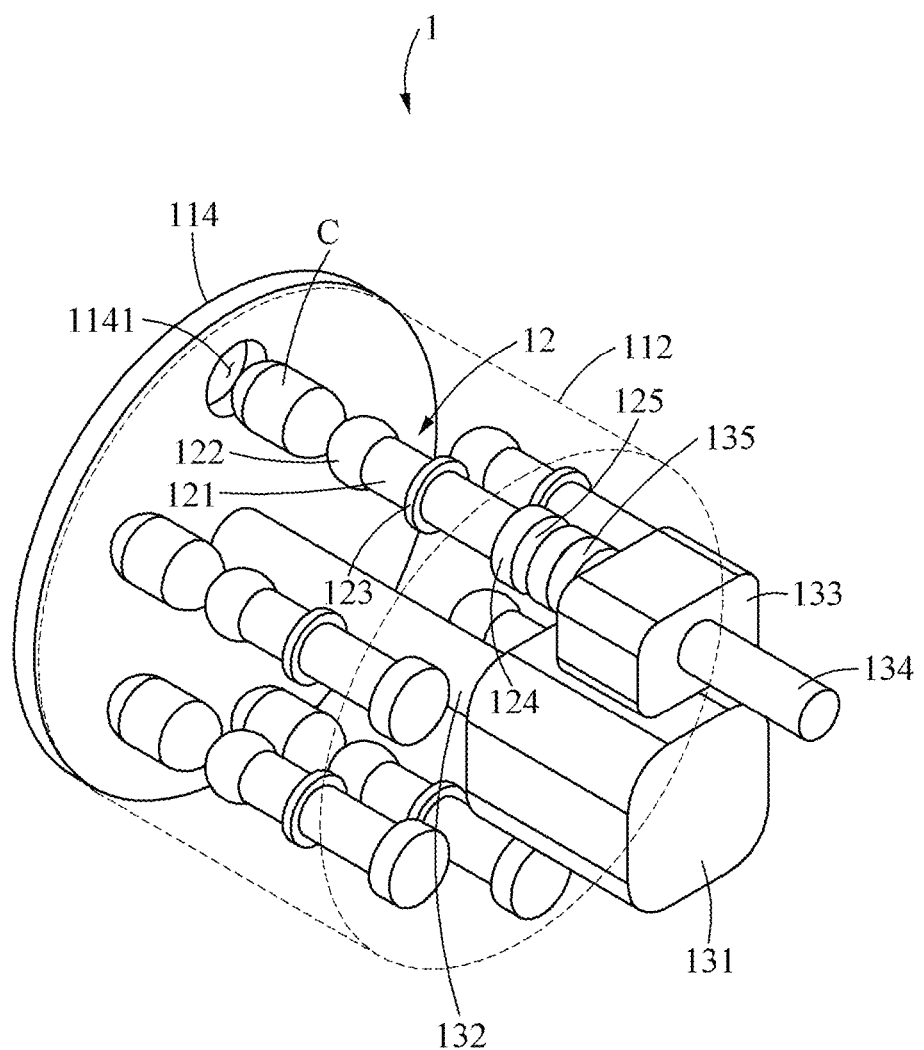
FIGS. 3 and 4 illustrate a first state of a device for conveying a biological material according to an example embodiment.

FIGS. 3 and 4 illustrate a first state of a device for conveying a biological material according to an example embodiment.

Referring to FIGS. 3 and 4, one of the plurality of conveyors 12 may be selected, and the selected conveyor 12 may be aligned with the aperture 1141. In this example, the aperture 1141 may also be aligned with the linear guide 134. When the selected conveyor 12 is aligned with the aperture 1141, the linear guide 134 may move toward the aperture 1141 in response to an operation of the linear driving element 133, such that the second magnetic element 135 may be coupled to the first magnetic element 125 provided in the second catch 124.

Figure 5:
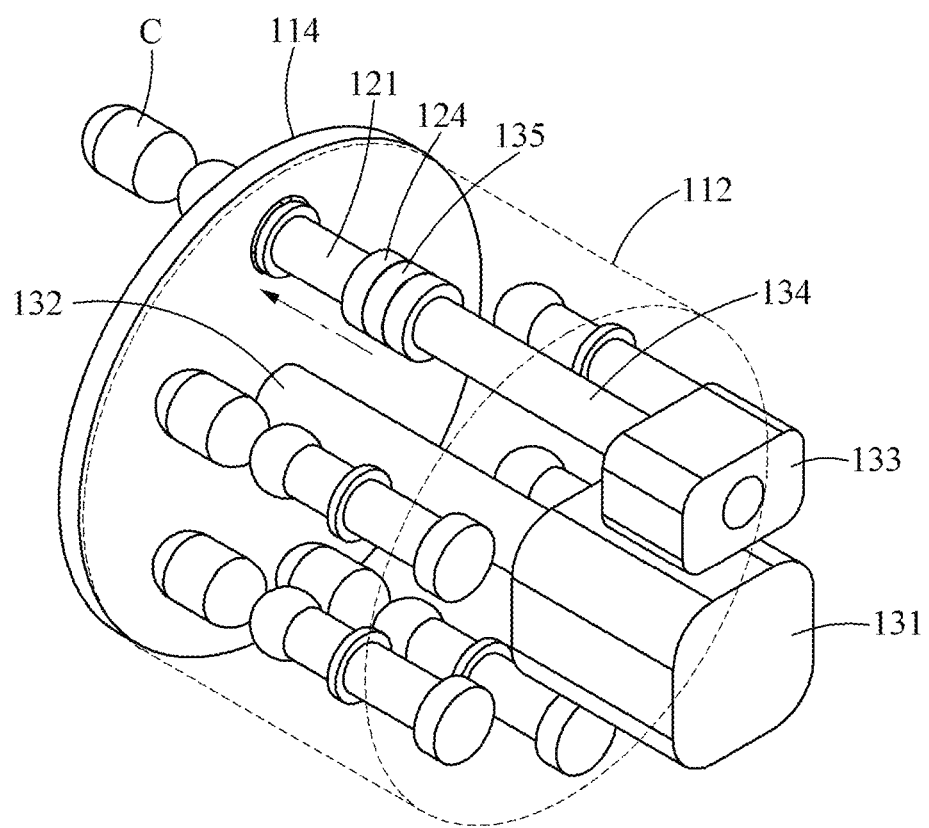
FIGS. 5 and 6 illustrate a second state of a device for conveying a biological material according to an example embodiment.
Figure 6:
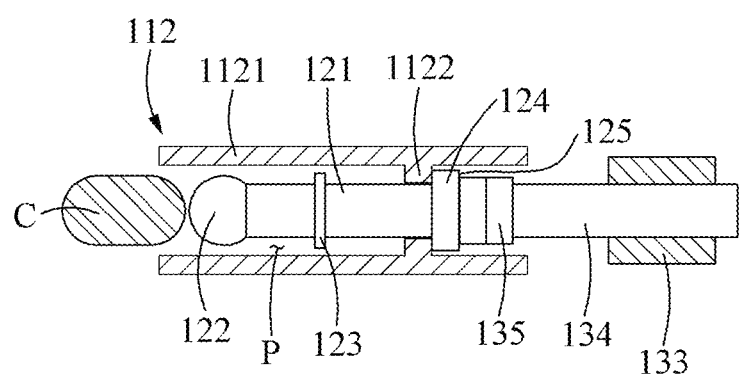

FIGS. 5 and 6 illustrate a second state of a device for conveying a biological material according to an example embodiment.

Referring to FIGS. 5 and 6, when the linear driving element 133 continuously operates in a situation in which the first magnetic element 125 of the second catch 124 and the second magnetic element 135 provided at the end portion of the linear guide 134 are coupled, the linear guide 134 may continuously move toward the aperture 1141, and a portion of the rod 121 and the conveying element 122 may move out of the second chamber 112 through the aperture 1141, such that the capsule C may be pushed out of the second chamber 112. Thereafter, a material contained in the capsule C pushed out of the second chamber 112 may be transferred to a desired site of the target. In this process, the second catch 124 may be caught by the stopper 1122 formed on the inner wall 1121 of the second chamber 112, such that the rod 121 and the conveying element 122 may not move forward any further. Thereafter, the conveying element 122 may collect a biological material at a desired site of the target while being sufficiently exposed to an outside of the second chamber 112.

Figure 7:
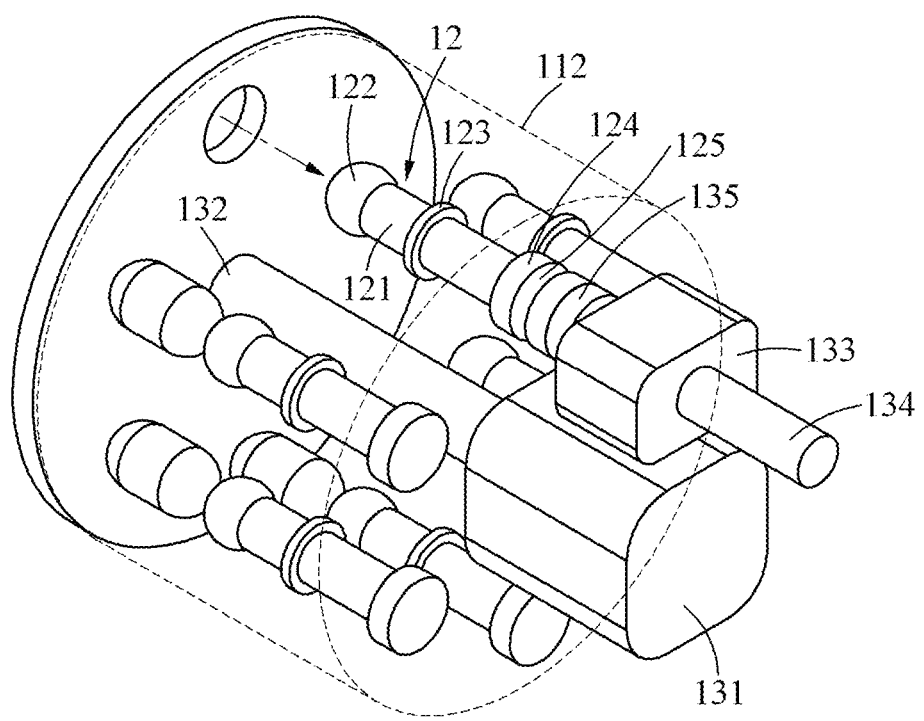
FIGS. 7 and 8 illustrate a third state of a device for conveying a biological material according to an example embodiment.
Figure 8:
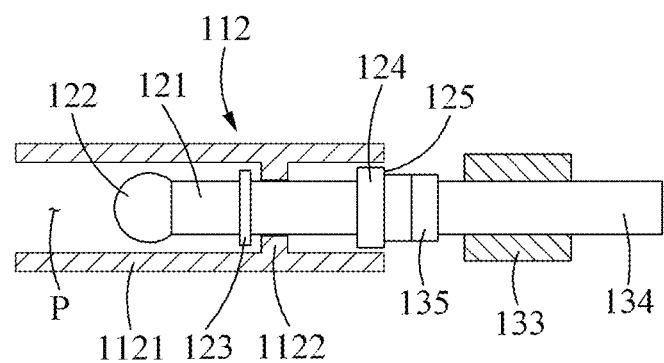

FIGS. 7 and 8 illustrate a third state of a device for conveying a biological material according to an example embodiment.

Referring to FIGS. 7 and 8, when the conveying element 122 collects a biological material from a desired part of the target while sufficiently exposed to the outside of the second chamber 112, the conveyor 12 may return to the inside of the second chamber 112. In detail, the linear driving element 133 may generate linear power in an opposite direction, the linear guide 134 may move back from the aperture, and the rod 121 and the conveying element 122 may also move back from the aperture together and return to the inside of the second chamber 112. In this process, the first catch 123 may be caught by the stopper 1122 formed on the inner wall 1121 of the second chamber 112, such that the rod 121 and the conveying element 122 may not move backward any further.

Thereafter, the biological material collected by the conveying element 122 may be stored in the second chamber 112.

As described above, the device for conveying a biological material may transfer a desired material to a desired site of the target and collect a biological material from a desired site of the target. Meanwhile, it may be understood that even in an example in which the capsule C is absent, the conveyor 12 may approach a biological material outside of the second chamber 112, collect the biological material, and move to store the collected biological material in the second chamber 112.

Figure 9:
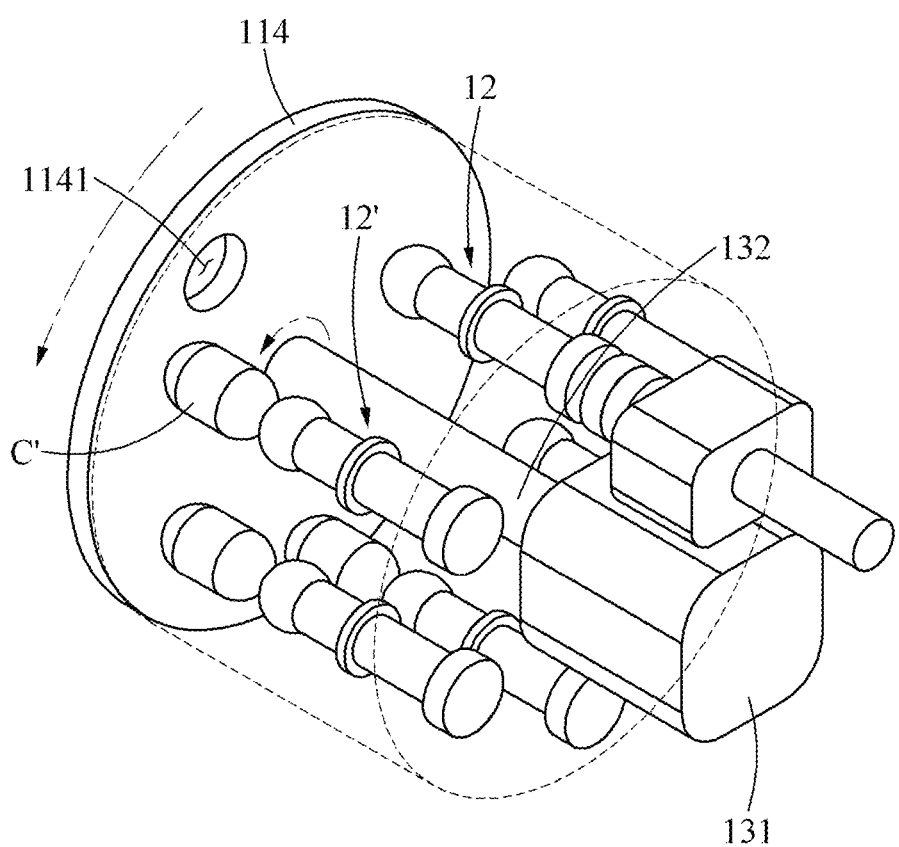
FIG. 9 is a perspective view illustrating a fourth state of a device for conveying a biological material according to an example embodiment.

FIG. 9 is a perspective view illustrating a fourth state of a device for conveying a biological material according to an example embodiment.

Referring to FIG. 9, when the rotation driving element 131 rotates the rotating shaft 132 counterclockwise, the plate 114 connected to the rotating shaft 132 may rotate together with the rotating shaft 132, such that the aperture 1141 may be repositioned. The aperture 1141 may be repositioned to be aligned with another conveyor 12', not the conveyor 12 that returned, to transfer a new capsule C' or to collect a new biological material. In this example, the positions of the plurality of conveyors 12 and 12' may be fixed.

Meanwhile, while the body 11 of the device 1 of the biological material is moving, the range of rotation of the plate 114 may be determined such that none of the plurality of conveyors 12 and 12' may be aligned with the aperture 1141, as shown in FIG. 9. Thus, the plurality of conveyors 12 and 12' may be protected not to be exposed to the outside of the body 11.

Figure 10:
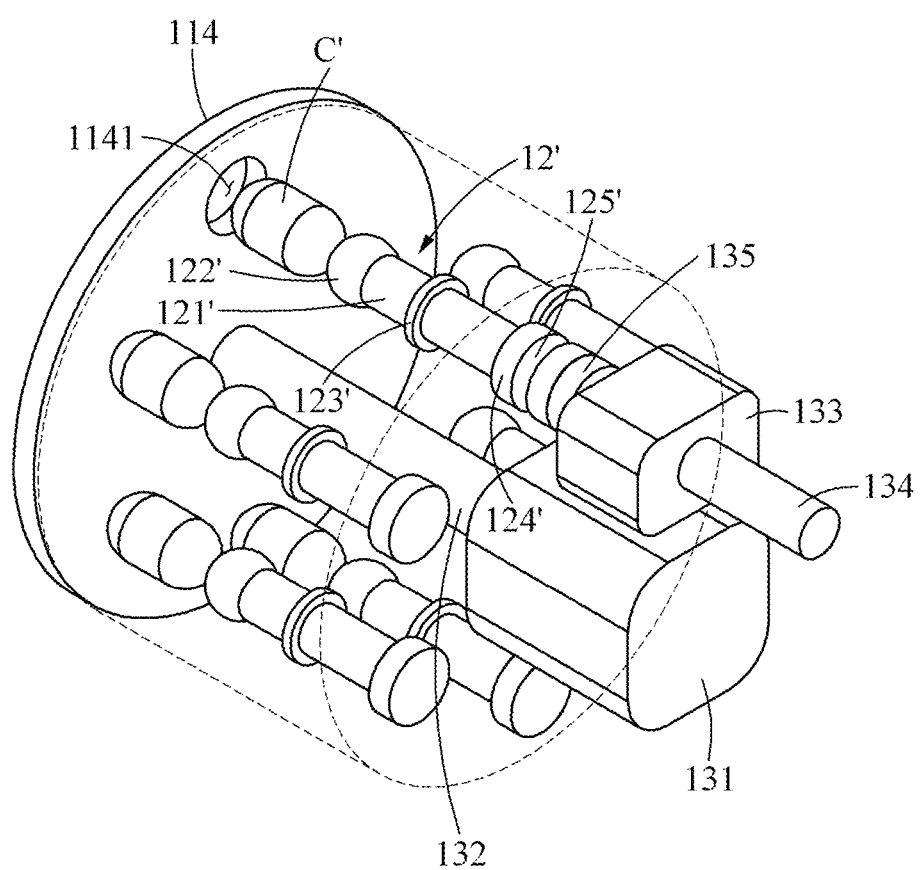
FIG. 10 is a perspective view illustrating a fifth state of a device for conveying a biological material according to an example embodiment.

FIG. 10 is a perspective view illustrating a fifth state of a device for conveying a biological material according to an example embodiment.

Referring to FIG. 10, another conveyor 12' may be aligned with the aperture 1141 together with the linear driving element 133 and the linear guide 134. Thereafter, in the same manner as described above with reference to FIGS. 3 through 8, the conveyor 12' may transfer a new capsule C' to a desired site of the target and collect a biological material from a desired site of the target.

Figure 11:
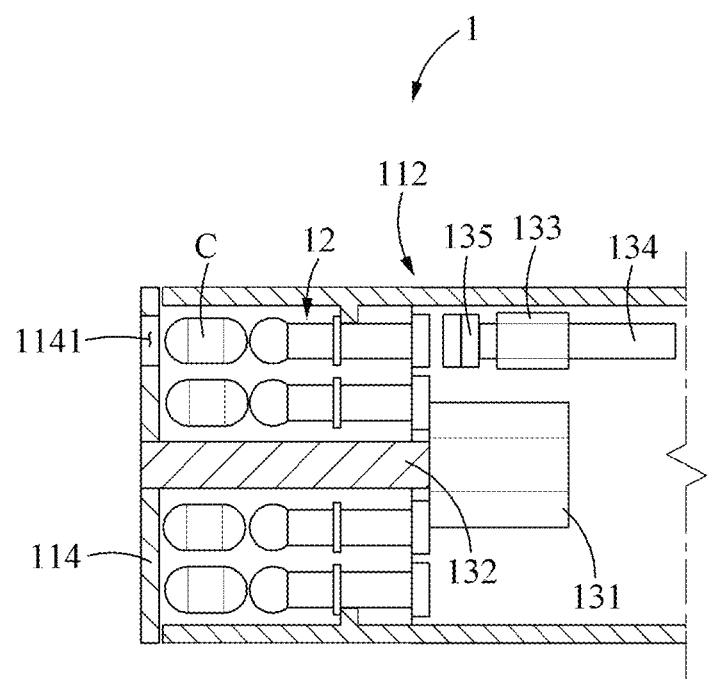
FIG. 11 is a cross-sectional view illustrating a first structure of a device for conveying a biological material according to an example embodiment.

FIG. 11 is a cross-sectional view illustrating a first structure of a device for conveying a biological material according to an example embodiment.

Referring to FIG. 11, the rotation driving element 131, the rotating shaft 132, and the plate 114 may be connected to each other as a single module. In this example, the rotating shaft 132 and the second chamber 112 may be connected in the form of a one-way clutch. In detail, when the rotation driving element 131 generates rotational power in a first direction, the rotating shaft 132 may rotate in the first direction, such that the plate 114, the second chamber 112, the linear driving element 133, and the linear guide 134 may rotate in the first direction together. Conversely, when the rotation driving element 131 generates rotational power in a second direction, which is an opposite direction of the first direction, the rotating shaft 132 may rotate in the second direction, such that the plate 114 may rotate in the second direction, whereas the second chamber 112 may not rotate.

Meanwhile, this structure may be used to select one of the plurality of conveyors 12 or to protect the plurality of conveyors 12. For example, to select one of the plurality of conveyors 12 and align the selected conveyor 12 with the aperture 1141, the rotation driving element 131 may generate rotational power in the first direction, whereby the plate 114, the second chamber 112, the linear driving element 133, and the linear guide 134 may rotate in the first direction together, and thus another conveyor 12 may be aligned with the aperture 1141, the plate 114, the second chamber 112, the linear driving element 133, and the linear guide 134. In another example, to protect the plurality of conveyors 12 from the outside of the second chamber 112, the rotation driving element 131 may generate rotational power in the second direction, whereby the plate 114 may rotate in the second direction whereas the second chamber 112 may not rotate, such that the aperture 1141 may be aligned with none of the plurality of conveyors 12.

Figure 12:
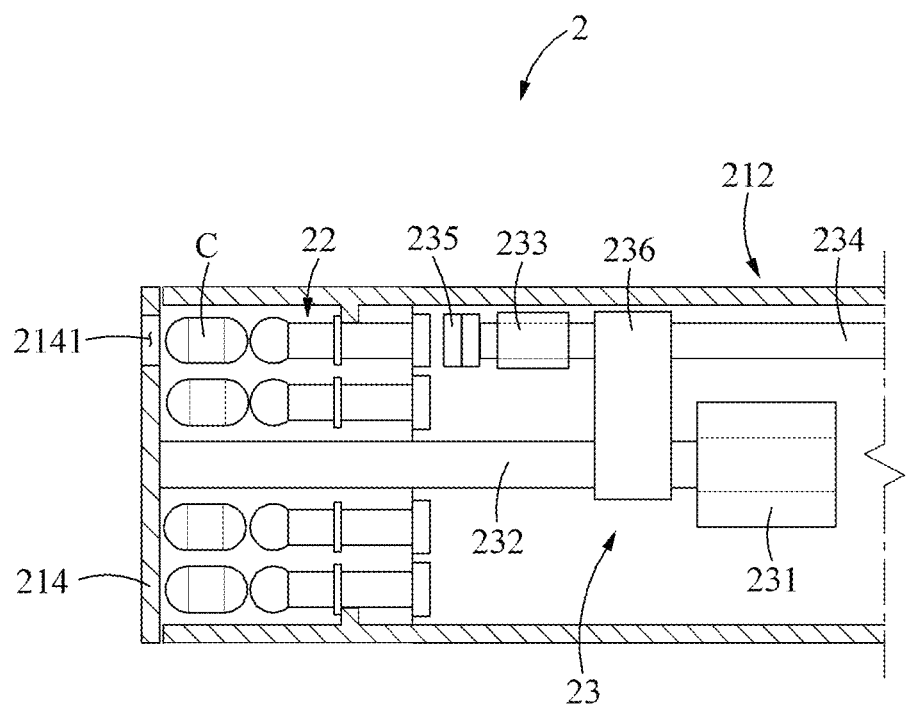
FIG. 12 is a cross-sectional view illustrating a second structure of a device for conveying a biological material according to an example embodiment.

FIG. 12 is a cross-sectional view illustrating a second structure of a device for conveying a biological material according to an example embodiment.

Referring to FIG. 12, a device 2 for conveying a biological material may include a power unit 23 of another structure. The power unit 23 may include a rotation driving element 231, a rotating shaft 232, a linear driving element 233, a linear guide 234, a magnetic element 235, and a connector 236 connecting the linear guide 234 and the rotating shaft 232.

The rotation driving element 231, a plate 214, and the linear driving element 233 may be connected to each other as a single module. In this structure, to cause a relative rotational motion, the rotating shaft 232 and the plate 214 may be connected to each other, and a second chamber 212 and a linear module including the linear driving element 233, the linear guide 234 and the magnetic element 235 may be connected to each other. When the rotation driving element 231 generates rotational power in any direction, the plate 214 may rotate such that an aperture 2141 may be aligned with the linear module including the linear driving element 233, the linear guide 234 and the magnetic element 235. In this example, the second chamber 212 may not rotate. In this manner, by generating rotational power in any direction through the rotation driving element 231, one of a plurality of conveyors 22 may be selected.

Figure 13:
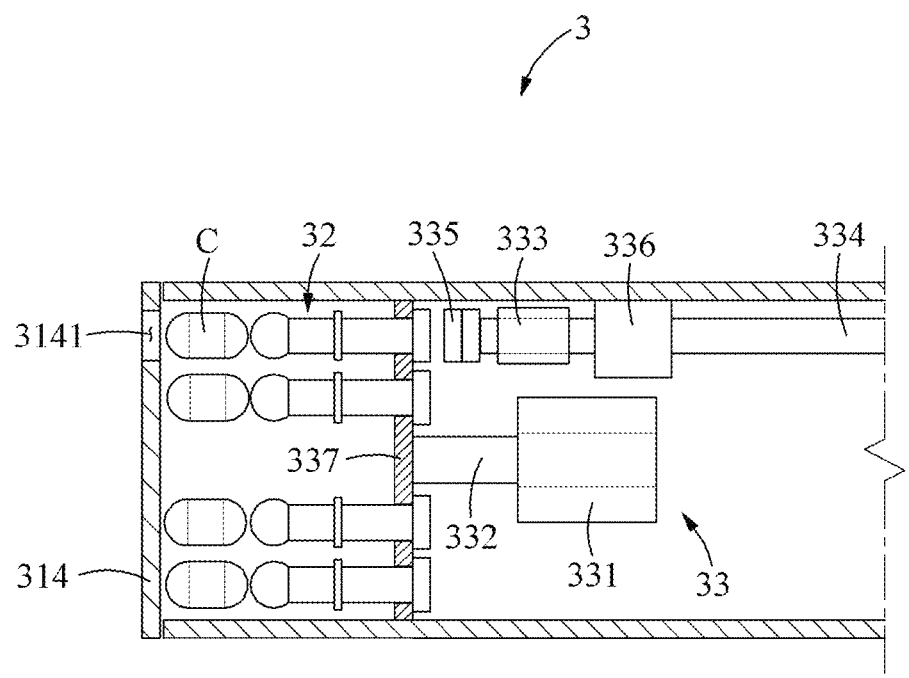
FIG. 13 is a cross-sectional view illustrating a third structure of a device for conveying a biological material according to an example embodiment.

FIG. 13 is a cross-sectional view illustrating a third structure of a device for conveying a biological material according to an example embodiment.

Referring to FIG. 13, a device 3 for conveying a biological material may include a power unit 33 of still another structure. The power unit 33 may include a rotation driving element 331, a rotating shaft 332, a linear driving element 333, a linear guide 334, a magnetic element 335, a fixer 336 configured to fix the linear guide 334 to a body of the device 3, and an additional second plate 337 to be rotated by the rotating shaft 332.

A plurality of conveyors 32 may be provided in the periphery of the second plate 337 to be arranged in a circumferential direction. When the rotation driving element 331 generates rotational power, the rotating shaft 332 may rotate in a direction in which the power is generated, such that the second plate 337 may rotate. In this example, positions of a first plate 314, the linear driving element 333, the linear guide 334 and the magnetic element 335 may be fixed, and thus depending on the range of rotation of the second plate 337, one of the plurality of conveyors 32 may be aligned with an aperture 3141, or none of the conveyors 32 may be aligned with the aperture 3141.

Figure 14:
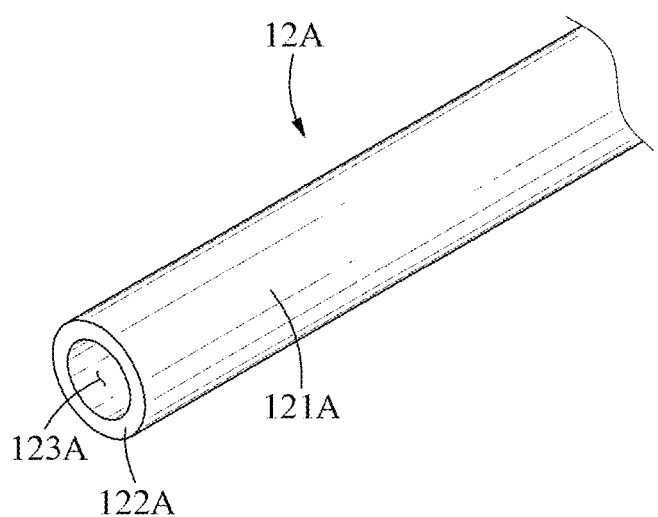
FIG. 14 is a partial perspective view illustrating a first structure of a conveyor according to an example embodiment.

FIG. 14 is a partial perspective view illustrating a first structure of a conveyor according to an example embodiment.

Referring to FIG. 14, a conveyor 12A may inhale a biological material. The conveyor 12A may include a rod 121A, a sucker 122A, and an inhaling aperture 123A. The sucker 122A may attach to a desired site of the target. The sucker 122A may be provided at an end portion of the rod 121A. The inhaling aperture 123A may inhale a biological material from a desired site of the target. The inhaling aperture 123A may be formed at the center of the end portion of the rod 121A and surrounded by the sucker 122A.

In an additional example, similar to the example described above with reference to FIG. 2, a capsule C containing a material may be transferred to a desired site of the target through the aperture 1141, while being gripped at the end portion of the rod 121A by a suction force through the inhaling aperture 123A.

Figure 15:
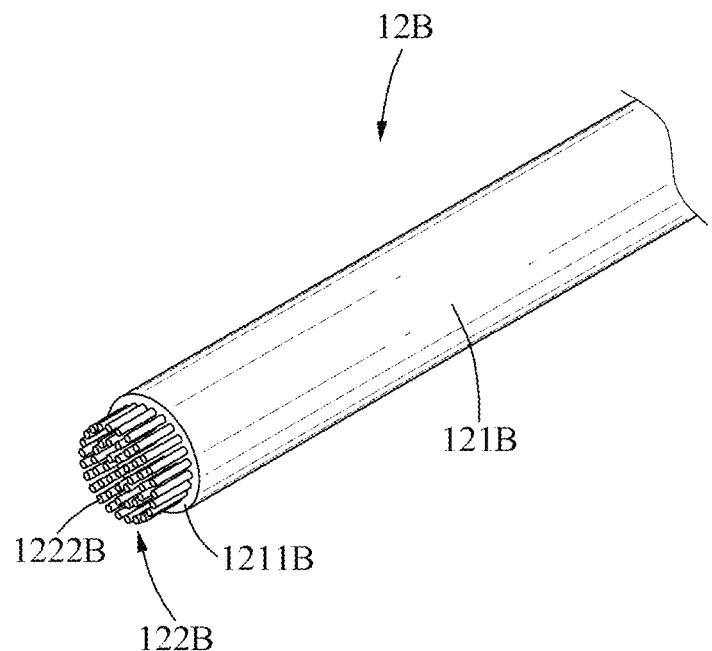
FIG. 15 is a partial perspective view illustrating a second structure of a conveyor according to an example embodiment.

FIG. 15 is a partial perspective view illustrating a second structure of a conveyor according to an example embodiment.

Referring to FIG. 15, a conveyor 12B may collect a biological material from a desired site of the target. The conveyor 12B may include a rod 121B, and a brush 122B formed at an end portion 1211B of the rod 121B. The brush 122B may collect the biological material. The brush 122B may include a plurality of scrubbing elements 1222B extending from the end portion 1211B of the rod 121B. A structure of the brush 122B having the plurality of scrubbing elements 1222B may lightly touch the site of the target, thereby collecting a desired biological material without damaging the site of the target. In addition, as in the example described above with reference to FIG. 2, the brush 122B may push a capsule C containing a material and transfer the capsule C to a desired site of the target through the aperture 1141.

Figure 16:
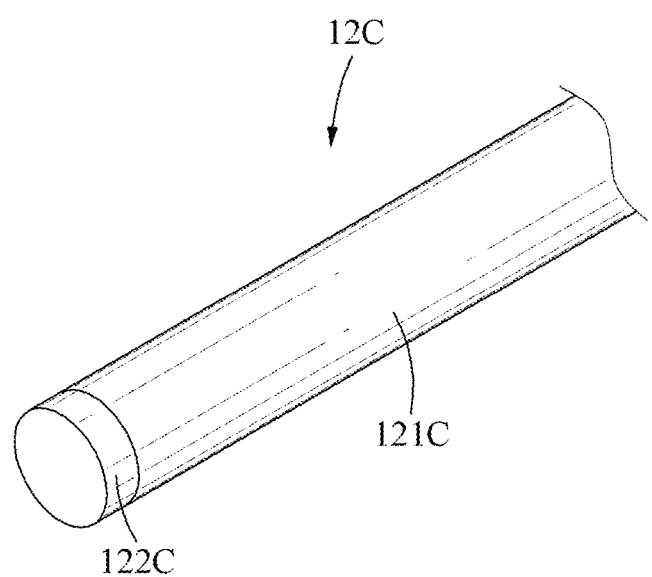
FIG. 16 is a partial perspective view illustrating a third structure of a conveyor according to an example embodiment.

FIG. 16 is a partial perspective view illustrating a third structure of a conveyor according to an example embodiment.

Referring to FIG. 16, a conveyor 12C may include a rod 121C, and an adhesive element 122C provided at an end portion of the rod 121C. The adhesive element 122C may collect a biological material by adhesion. For example, the adhesive element 122C may be provided in the form of gel.

Figure 17:
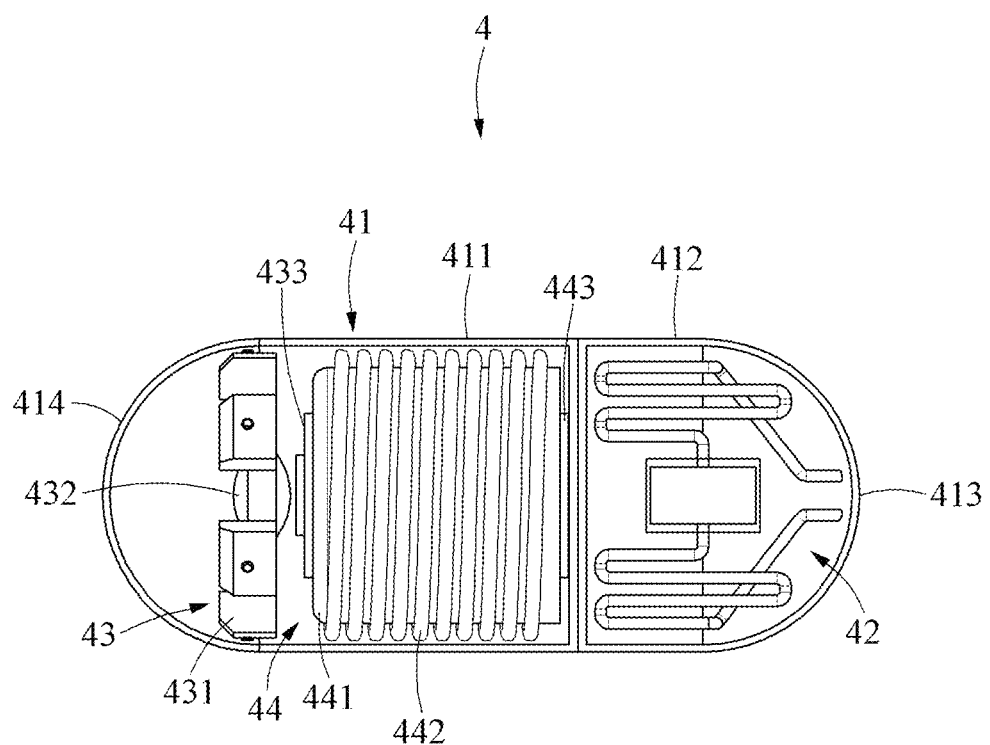
FIG. 17 is a cross-sectional view illustrating a device for conveying a biological material according to an example embodiment.

FIG. 17 is a cross-sectional view illustrating a device for conveying a biological material according to an example embodiment.

Referring to FIG. 17, a conveying device 4 may move along a lumen of a target to collect a biological material from a desired site of the target or to transfer a biological material to a desired site of the target.

The conveying device 4 may include a body 41, a convey assembly 42, an optical assembly 43, and a circuit 44.

The body 41 may move along the lumen of the target. The body 41 may be provided in the shape of a capsule. This shape of the body 41 may help the target to easily accept oral administration of the conveying device 4.

The body 41 may be provided in the size appropriate to move along the lumen of the target. In an example, the width of the body 41 may be about 0.3 mm to about 12 mm, preferably, about 1 mm to 11 mm. In this example, the length of the body 41 may be about 0.75 mm to about 30 mm, preferably, about 2 mm to about 29 mm.

The body 41 may include a first chamber 411 with a first end portion 414, and a second chamber 412 with a second end portion 413. The first chamber 411 may include a cavity configured to accommodate the optical assembly 43 and the circuit 44. The first chamber 411 may be provided in the shape of a substantially hollow cylinder. However, the shape of the first chamber 411 is not limited thereto. The second chamber 412 may include a cavity configured to accommodate the convey assembly 42. In an example, the volume of the first chamber 411 may be greater than the volume of the second chamber 412.

The first chamber 411 and the second chamber 412 may be arranged in a row in a longitudinal direction of the body 41. In this example, the first end portion 414 and the second end portion 413 may respectively correspond to a tip portion and a rear end portion of the body 41. However, example embodiments are not limited thereto. The first end portion 414 and the second end portion 413 may respectively correspond to the rear end portion and the tip portion. That is, the body 41 may move in a direction that the first end portion 414 faces, or move in a direction that the second end portion 413 faces.

The first chamber 411 and the second chamber 412 may be detachable from each other. In an example, a wall of the first chamber 411 and a wall of the second chamber 412 may be coupled to each other. In another example, a single separating wall may be formed between the first chamber 411 and the second chamber 412.

The first chamber 411 and the second chamber 412 may have substantially the same width. Here, the "width" refers to a maximum distance from one side of the element to the other side. For example, when the first chamber 411 and the second chamber 412 each have a circular cross section, the width thereof may be the diameter thereof.

The convey assembly 42 may collect a biological material from a target site outside of the body 41, transfer a biological material to a target site outside of the body 41, or perform all the operations. The convey assembly 42 may be detachable from the second chamber 412.

The optical assembly 43 may acquire an image of a surrounding environment of the body 41. The optical assembly 43 may include a light emitting diode (LED) 431, a lens 432, and a camera 433. The LED 431 may emit an optical signal to the surrounding environment of the body 41. The lens 432 may receive the optical signal from the surrounding environment of the body 41 and transfer the same to the camera 433. The camera 433 may receive the optical signal received by the lens 432, and generate an image with respect to the surrounding environment of the body 41. In an example, the lens 432 may be disposed at a central axis extending along the longitudinal direction of the body 41, and the LED 431 may be disposed around the lens 432. In an example, a plurality of LEDs 431 may be provided. The optical assembly 43 may be detachable from the first chamber 411.

The convey assembly 42 and the optical assembly 43 may be respectively assembled with the first chamber 411 and the second chamber 412. When the convey assembly 42 and the optical assembly 43 are respectively assembled with the first chamber 411 and the second chamber 412, the first chamber 411 and the second chamber 412 may block exposure of the convey assembly 42 and the optical assembly 43 to the outside.

The circuit 44 may include an electric energy storing element 441, a communication element 442, and a control element 443. The electric energy storing element 441 may supply electric energy to the convey assembly 42 and the optical assembly 43. For example, the electric energy storing element 441 may include a battery. The communication element 442 may communicate with a computer outside of the conveying device 4. The communication element 442 may include a signal generator configured to generate an externally recognizable position signal. The position of the conveying device 4 may be detected based on the position signal generated by the signal generator. For example, the communication element 442 may generate an RF signal. In another example, the communication element 442 may generate a magnetic field. The communication element 442 may be implemented by an antenna, a permanent magnet, or an electromagnet. The control element 443 may control a movement of the body 41, an operation of the convey assembly 42, and an operation of the optical assembly 43. For example, the control element 443 may include a circuit board.

The conveying device 4 may be detected by an external signal in the lumen of the target. In an example, the position of the conveying device 4 in the lumen of the target may be detected by an external X-ray. In another example, the position of the conveying device 4 in the lumen of the target may be detected by an external ultrasonic wave. The position of the conveying device 4 may be detected in real time in the manners described above. When the conveying device 4 reaches a desired site of the target through appropriate control, the conveying device 4 may transfer a biological material to the target site, or collect a biological material from the site.

Figure 18:
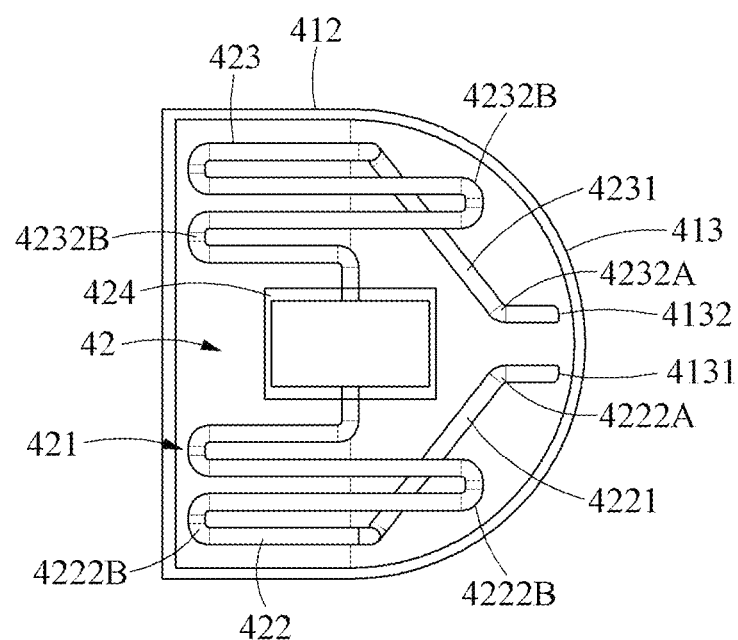
FIG. 18 is a cross-sectional view illustrating a convey assembly of the device of FIG. 17.
Figure 19:
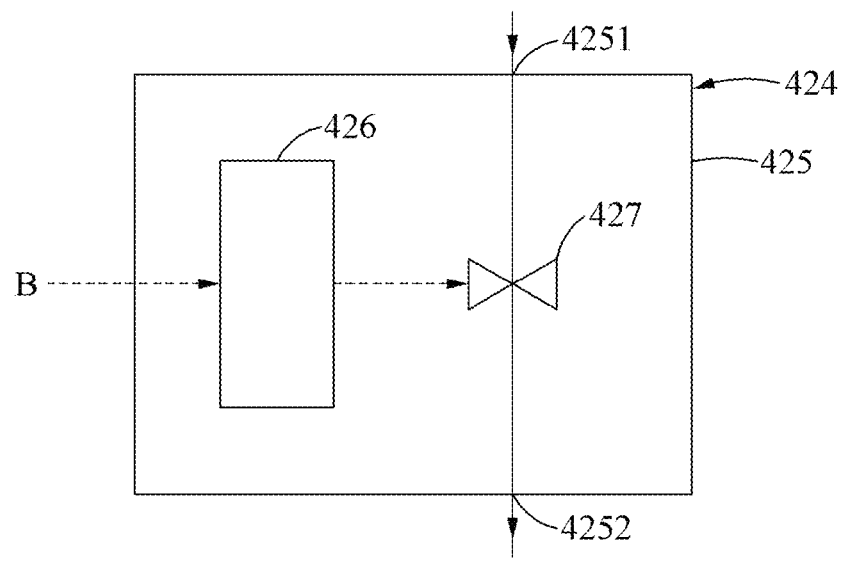
FIG. 19 illustrates a structure of a pump of the convey assembly of FIG. 18.
Figure 20:
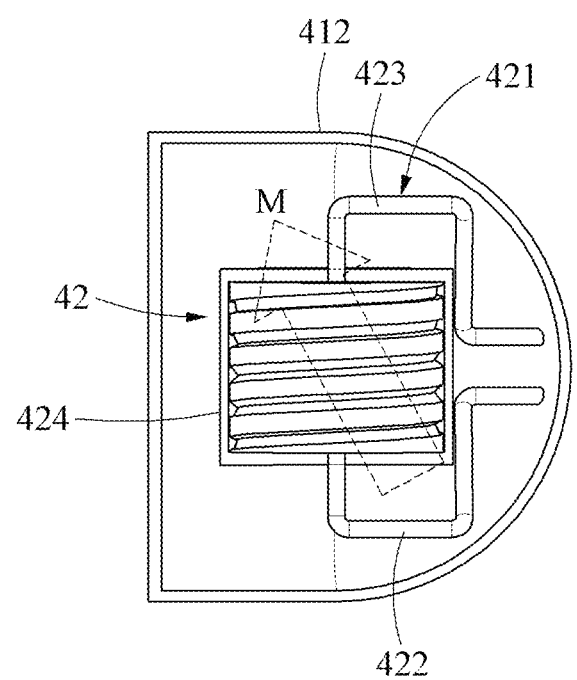
FIG. 20 is a cross-sectional view illustrating a convey assembly according to an example embodiment.
Figure 21:
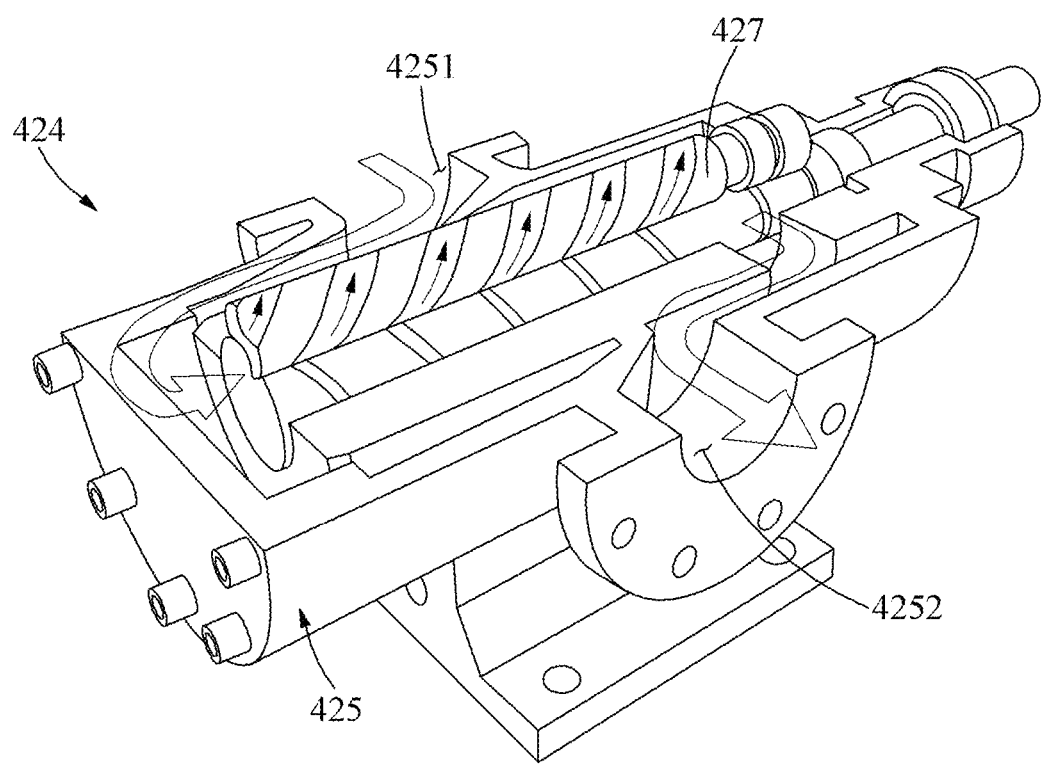
FIG. 21 illustrates an operation of the convey assembly of FIG. 20.

FIG. 18 is a cross-sectional view illustrating a convey assembly of the device of FIG. 17.

Referring to FIG. 18, the second chamber 412 may include a channel inlet 4131 and a channel outlet 4132. The channel inlet 4131 may allow an entry of a biological material from an outside of the second chamber 412. The channel outlet 4132 may allow an exit of the biological material or a medium fluid, which will be described later, to the outside of the second chamber 412.

The convey assembly 42 may include a channel 421 and a pump 424. The channel 421 may connect the channel inlet 4131 and the channel outlet 4132. The channel 421 may store the biological material collected from the outside of the second chamber 412. The pump 424 may pump the biological material or the medium fluid from the channel inlet 4131 through the channel 421 to the channel outlet 4132.

The channel inlet 4131 and the channel outlet 4132 may be formed on the same side of the second chamber 412. In an example, the channel inlet 4131 and the channel outlet 4132 may be formed in the second end portion 413 of the second chamber 412.

The channel inlet 4131 and the channel outlet 4132 may be adjacent to each other. By this structure, when the medium fluid is discharged through the channel outlet 4132, a mixed fluid of the biological material outside of the convey assembly 42 and the discharged medium fluid may easily enter the channel inlet 4131.

In an alternative example, the channel inlet 4131 and the channel outlet 4132 may be at a sufficient distance and spaced apart from each other. By this structure, a biological material may be transferred exactly to a target site, without entering the channel inlet 4131.

The channel 421 may contain the medium fluid. The medium fluid may include a predetermined, appropriate fluid having no effect on a biological material. For example, the medium fluid may include physiological saline, distilled water (DI-water), phosphate buffer saline, and other culture media. The medium fluid may be mixed with a biological material. When the medium fluid and a biological material are mixed, the mixture may have a viscosity within a predetermined range. The mixture may have a viscosity within a predetermined range appropriate for inhalation or discharge of the mixture. Before the convey assembly 42 operates, the channel 421 may be filled with the medium fluid.

The pump 424 may be disposed on the channel 421. The channel 421 may include a first passage 422 and a second passage 423. The first passage 422 may connect the channel inlet 4131 and an inlet port of the pump 424. The second passage 423 may connect an outlet port of the pump 424 and the channel outlet 4132.

The first passage 422 may include a first tubular element 4221 and a plurality of first bent portion 4222A and 4222B formed in the first tubular element 4221, and the second passage 423 may include a second tubular element 4231 and a plurality of second bent portion 4232A and 4232B formed in the second tubular element 4231. The number of the first bent portion 4222A and 4222B and the number of the second bent portion 4232A and 4232B may be predetermined to be appropriate numbers based on the volume of the second chamber 412 and the disposition of the pump 424. These meandering shapes of the first passage 422 and the second passage 423 may be space-efficient to store a biological material in the channel 421.

In a preferable example, one of the plurality of first bent portion 4222A and 4222B, for example, the first bent portion 4222A, may be adjacent to the channel inlet 4131, and one of the plurality of second bent portion 4232A and 4232B, for example, the second bent portion 4232A, may be adjacent to the channel outlet 4132. This arrangement of the first bent portion 4222A and the second bent portion 4232A may block an undesired entry of the biological material through the channel inlet 4131 and an undesired exit of the biological material through the channel outlet 4132.

The pump 424 may discharge at least a portion of the medium fluid contained in the channel 421 through the channel outlet 4132 toward a target having a biological material. The portion of the medium fluid discharged through the channel outlet 4132 may be mixed with the biological material of the target. Thus, a mixture of the discharged medium fluid and the biological material may be formed. When the pump 424 operates, the mixture may be inhaled into the channel 421 through the channel inlet 4131. Alternatively, the channel 421 may not contain a medium fluid. In this example, the pump 424 may discharge the biological material in the channel 421 through the channel outlet 4132 to the outside of the second chamber 412 without using a medium fluid, or inhale the biological material into the channel 421 without using a medium fluid.

The pump 424 may repeat discharging at least a portion of the medium fluid contained in the channel 421 and inhaling the mixture formed outside of the second chamber 412. Thus, various types of biological materials may be stored in the channel 421. When biological materials are sufficiently collected in the channel 421, the operation of the pump 424 may be stopped. The biological material in the channel 421 may be obtained when the conveying device 4 is removed from a body of the target.

The flow volume of the second passage 423 may be less than the flow volume of the first passage 422. In an example, the pump 424 may be disposed more adjacent to the channel outlet 4132, than the channel inlet 4131. In this example, the total length of the second tubular element 4231 of the second passage 423 may be less than the total length of the first tubular element 4221 of the first passage 422. By this structure, the medium fluid may be discharged from the channel 421 to the outside of the convey assembly 42 through the channel outlet 4132, such that a biological material outside of the convey assembly 42 may be induced to enter the channel inlet 4131. That is, the biological material may be easily collected. In an alternative example, the pump 424 may be disposed such that the total length of the first tubular element 4221 may be substantially the same as the total length of the second tubular element 4231. This may be appropriate for the medium fluid in the channel 421 to transfer the biological material in the channel 421 to the outside of the convey assembly 42 by hydraulic pressure. In this example, the first passage 422 may contain the medium fluid, and the second passage 423 contain the biological material. In another example, the diameter of the second tubular element 4231 of the second passage 423 may be less than the diameter of the first tubular element 4221 of the first passage 422. This structure may enable a more amount of biological material to be stored in the channel 421.

FIG. 19 illustrates a structure of a pump of the convey assembly of FIG. 18.

Referring FIG. 19, the pump 424 may include a casing 425, a magnetic element 426, and a driving element 427.

The casing 425 may include an inlet port 4251 through which a material enters, and an outlet port 4252 through which the material exits. The casing 425 may be provided in any appropriate shape which may not interrupt the functions of the other elements.

The magnetic element 426 may receive an external magnetic field B and drive the driving element 427 based on the external magnetic field B. For example, the magnetic element 426 may include a permanent magnet having a set magnetization direction.

The driving element 427 may induce a material entering the inlet port 4251 to move to the outlet port 4252. The driving element 427 may operate in one of a first state in which connection of the channel is allowed and a second state in which connection of the channel is blocked or delayed, by means of the magnetic element 426.

Characteristics of the external magnetic field B applied to the magnetic element 426 may be controlled. For example, by controlling the size, the frequency, and the waveform of the external magnetic field B, independent and individual control of the driving element 427 may be enabled.

In an alternative example, the pump 424 may be driven in a manner other than the magnetic drive manner described above. The pump 424 may be driven by means of a mechanical actuator (not shown) configured to drive the pump 424 and the circuit 44 described above with reference to FIG. 17. For example, the mechanical actuator may include a rotary motor, a shape memory alloy actuator, a piezo actuator, and other actuators which are obvious to those skilled in the art.

FIG. 20 is a cross-sectional view illustrating a convey assembly according to an example embodiment, and FIG. 21 illustrates an operation of the convey assembly of FIG. 20.

Referring to FIGS. 20 and 21, the convey assembly 42 may include the channel 421 and the screw pump 424 having a set magnetization direction M. In this example, the driving element 427, that is, a screw, of the screw pump 424 may include a drive shaft. The screw may include a magnetic element affected by an external magnetic field, preferably, a rotating magnetic field or a reciprocating magnetic field. The magnetization direction M of the magnetic element of the screw may form a set angle with respect to an axial direction of the drive shaft of the screw. The external magnetic field may be formed about an axial direction of a central axis of the screw, such that the screw may rotate about the central axis.

When the screw being the driving element 427 rotates relative to the drive shaft, the biological material entering the inlet port 4251, the medium fluid, or a combination thereof may be guided along threads formed on the screw and discharged through the outlet port 4252. In this process, when the screw rotates, a negative pressure may be applied to the inlet port 4251, and a positive pressure may be applied to the outlet port 4252. Here, the inlet port 4251 and the outlet port 4252 may be respectively connected to the first passage 422 and the second passage 423.

Figure 22:
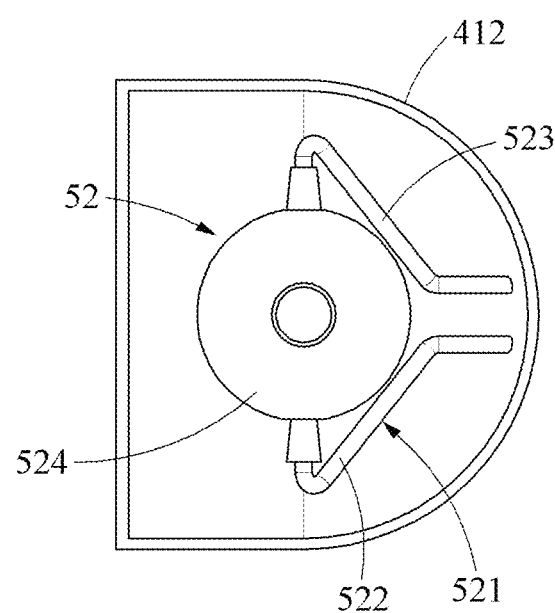
FIG. 22 is a cross-sectional view illustrating a convey assembly according to an example embodiment.
Figure 23:
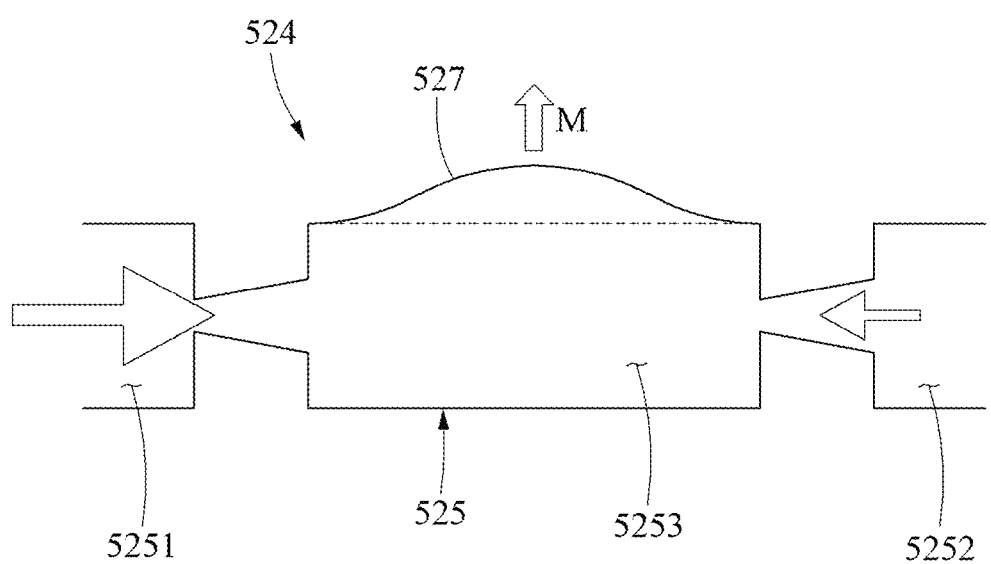
FIGS. 23 and 24 illustrate an operation of the convey assembly of FIG. 22.
Figure 24:
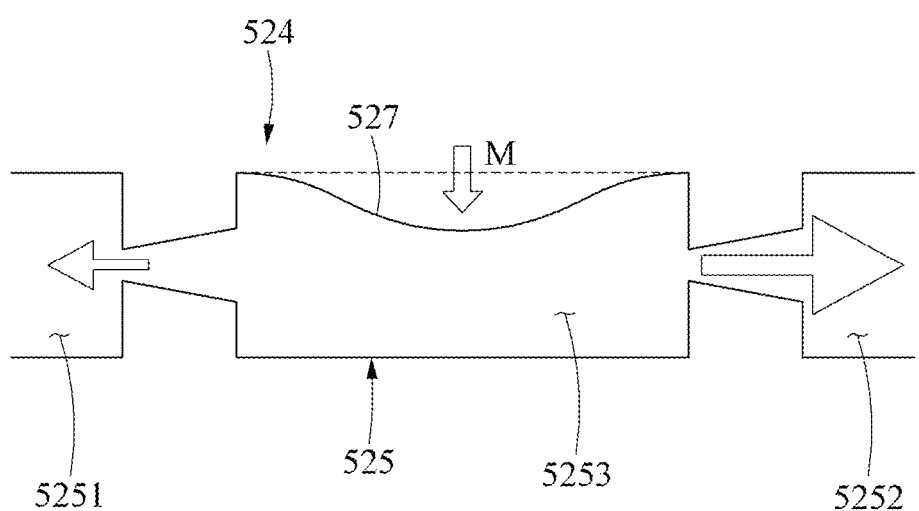

FIG. 22 is a cross-sectional view illustrating a convey assembly according to an example embodiment, and FIGS. 23 and 24 illustrate an operation of the convey assembly of FIG. 22.

Referring to FIGS. 22 through 24, a convey assembly 52 may include a channel 521 and a diaphragm pump 524 having a set magnetization direction M. Here, the magnetization direction M of the diaphragm pump 524 may be a vertical direction (in the example of FIGS. 23 and 24).

The diaphragm pump 524 may include a diffuser 525 having an inlet port 5251, an outlet port 5252 and an inner chamber 5253, and a deformable membrane 527 which is a driving element forming at least a portion of the inner chamber 5253 of the diffuser 525. When the membrane 527 moves in a vertical direction (in the example of FIG. 23), a material may be forced to move from the inlet port 5251 to the outlet port 5252. In this process, a negative pressure may be applied to the inlet port 5251, and a positive pressure may be applied to the outlet port 5252. Here, the inlet port 5251 and the outlet port 5252 may be respectively connected to a first passage 522 and a second passage 523.

The diaphragm pump 524 may include a magnetic element having the set magnetization direction M. When an external magnetic field is applied to the magnetic element, the movement and steering of a conveying device may be determined by a torque and a magnetic force by a gradient magnetic field. In an example not shown, the magnetic element may be provided in the membrane 527. In this example, the magnetic element provided in the membrane 527 may vibrate by means of the external magnetic field with a relatively low magnitude and a relatively high frequency, such that the material may move from the inlet port 5251 to the outlet port 5252.

Figure 25:
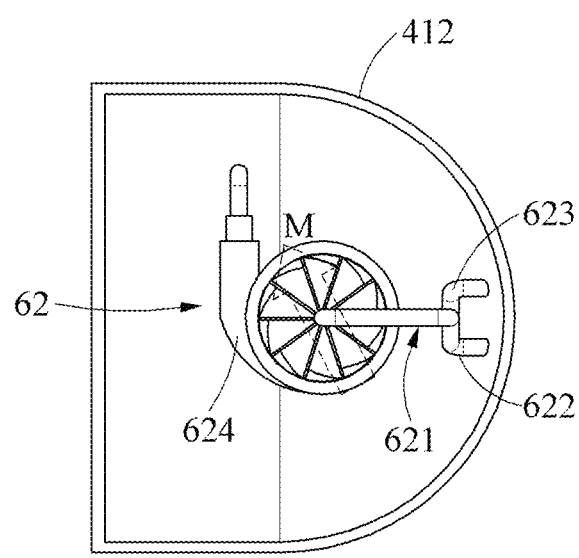
FIG. 25 is a cross-sectional view illustrating a convey assembly according to an example embodiment.
Figure 26:
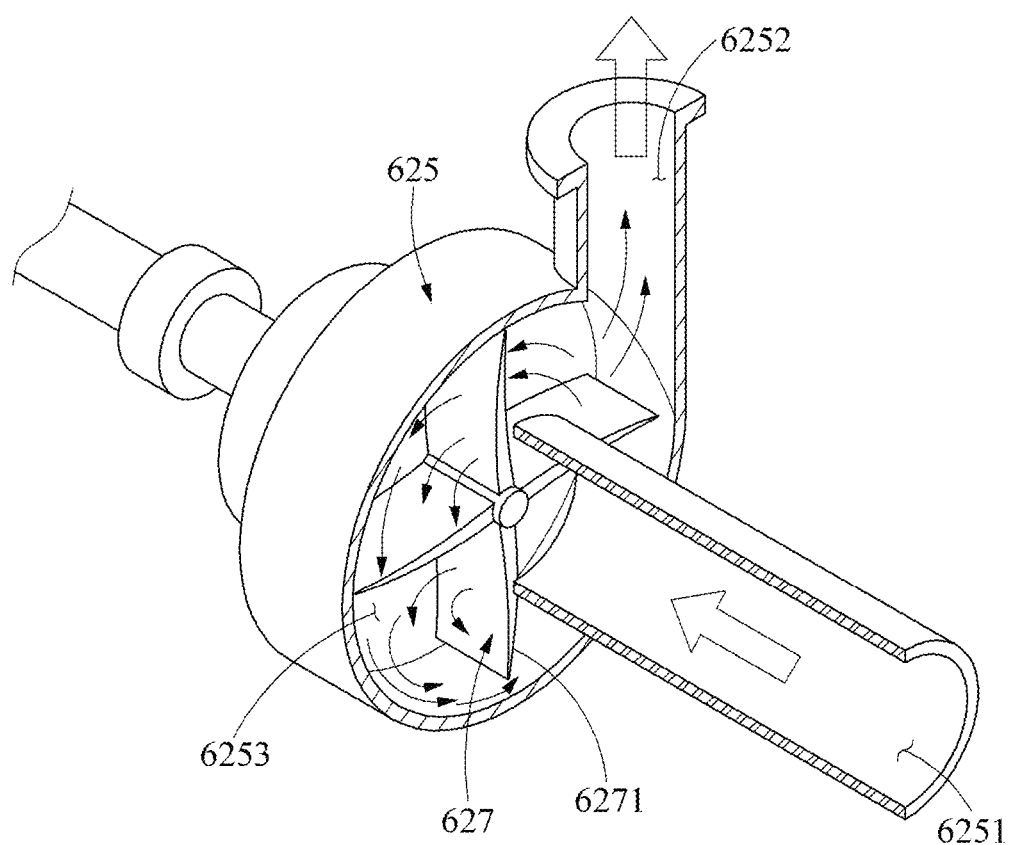
FIG. 26 illustrates an operation of the convey assembly of FIG. 25.

FIG. 25 is a cross-sectional view illustrating a convey assembly according to an example embodiment, and FIG. 26 illustrates an operation of the convey assembly of FIG. 25.

Referring to FIGS. 25 and 26, a convey assembly 62 may include a channel 621 and a centrifugal pump 624 having a set magnetization direction M. The centrifugal pump 624 may include a casing 625 having an inlet port 6251, an outlet port 6252 and an inner chamber 6253, and an impeller 627 which is a driving element having a plurality of blades 6271 configured to generate a flow as rotating in the inner chamber 6253. Here, the magnetization direction M may be a direction perpendicular to a rotation axis of the impeller 627. When the impeller 627 rotates, a fluid may be forced to flow by means of the plurality of blades 6271, such that a negative pressure may be applied to the inlet port 6251 and a positive pressure may be applied to the outlet port 6252. Here, the inlet port 6251 and the outlet port 6252 may be respectively connected to a first passage 622 and a second passage 623. A magnetic element having a magnetization direction M which forms a set angle with respect to an axial direction of the impeller 627 may be provided in the impeller 627. When an external magnetic field is applied to the magnetic element, the movement and steering of a conveying device may be determined by a torque and a magnetic force by a gradient magnetic field. Further, when a rotating magnetic field is applied about the axial direction of the impeller 627, the impeller 627 may rotate.

Figure 27:
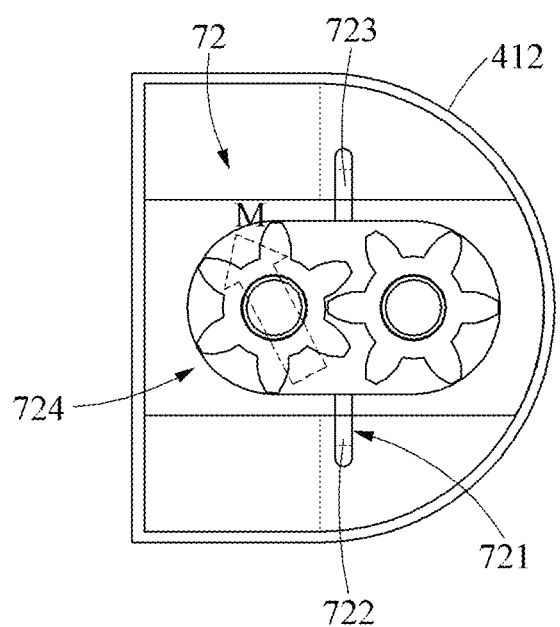
FIG. 27 is a cross-sectional view illustrating a convey assembly according to an example embodiment.
Figure 28:
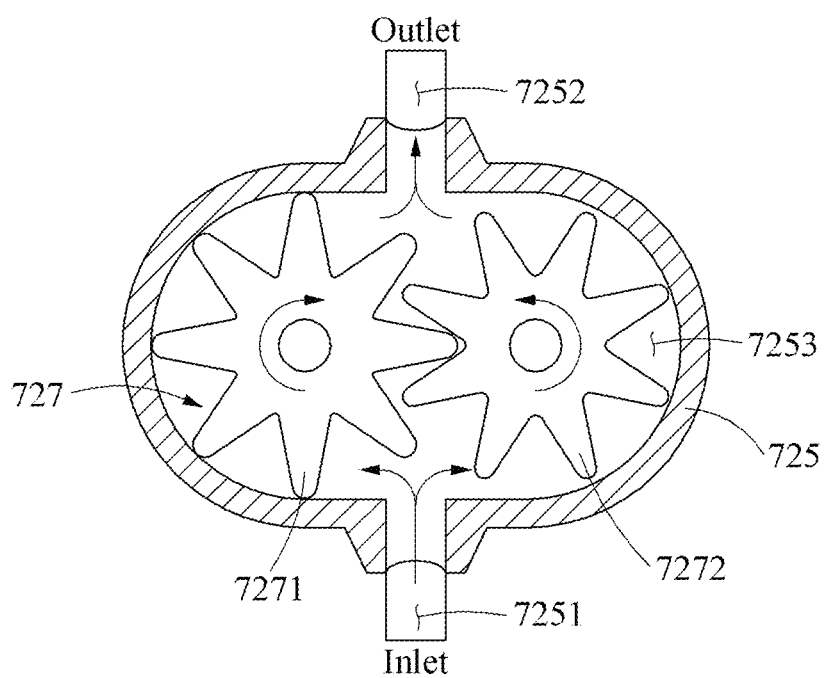
FIG. 28 illustrates an operation of the convey assembly of FIG. 27.

FIG. 27 is a cross-sectional view illustrating a convey assembly according to an example embodiment, and FIG. 28 illustrates an operation of the convey assembly of FIG. 27.

Referring to FIGS. 27 and 28, a convey assembly 72 may include a channel 721 and a gear pump 724 having a set magnetization direction M. The gear pump 724 may include a casing 725 having an inlet port 7251, an outlet port 7252 and an inner chamber 7253, and a driving element 727 having a first gear 7271 and a second gear 7272 which are rotatably provided in the inner chamber 7253 and configured to engage with each other. A magnetic element affected by an external magnetic field may be provided in at least one of the first gear 7271 and the second gear 7272. The magnetic element may have a magnetization direction M which forms a set angle with respect to an axial direction of a drive shaft of at least one of the first gear 7271 and the second gear 7272. When an external magnetic field is applied to the magnetic element, the first gear 7271 and the second gear 7272 may rotate, such that a negative pressure may be applied to the inlet port 7251, and a positive pressure may be applied to the outlet port 7252. Here, the inlet port 7251 and the outlet port 7252 may be respectively connected to a first passage 722 and a second passage 723. In this example, the applied magnetic field may be a rotating magnetic field which is generated about the drive shaft of at least one of the first gear 7271 and the second gear 7272 for the active rotation of the first gear 7271 and the second gear 7272. Further, when the external magnetic field is applied to the magnetic element, the steering and movement of a conveying device may be determined by a torque and a magnetic force by a gradient magnetic field.

According to example embodiments, a device may collect intestinal biological materials from many sites and transfer desired biological materials to many sites with a single diagnosis. Further, the device may effectively collect and safely store biological materials. In addition, the device may have a plurality of separate spaces, thereby achieving a compact structure.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A device for conveying a biological material, the device comprising:
- a body comprising an aperture configured to enable connection between an outside of the body and a chamber configured to store a biological material;
- a plurality of conveyors accommodated in the body and configured to convey the material; and
- a driver configured to select one conveyor of the plurality of conveyors, align the selected conveyor with the aperture, and move the selected conveyor to the outside of the body through the aperture;
- wherein the driver comprises a rotation driving element with a rotating shaft, and the plurality of conveyors is rotated about the rotating shaft relative to the body by means of the rotation driving element.

2. The device of claim 1, wherein the body further comprises a plate, and the plate comprises the aperture, defines a portion of the chamber, and is rotated by means of the rotation driving element.

3. The device of claim 2, wherein the rotation driving element is configured to rotate the plate relative to a rest of the body by rotating the rotating shaft in a first direction.

4. The device of claim 3, wherein the rotation driving element is configured to rotate the rest of the body and the plate together by rotating the rotating shaft in a second direction, which is an opposite direction to the first direction.

5. The device of claim 1, wherein the driver further comprises a second plate on which the plurality of conveyors is arranged in a circumferential direction, and the second plate is rotated by means of the rotation driving element.

6. The device of claim 1, wherein no conveyor of the plurality of conveyors is aligned with the aperture while the body is moving along a lumen of a target.

7. The device of claim 1, wherein the driver comprises:
- a linear driving element configured to move the selected conveyor toward the aperture or move the selected conveyor back from the aperture; and
- a linear guide configured to transfer a power generated by the linear driving element to the selected conveyor,
- wherein each conveyor of the plurality of conveyors comprises a first magnetic element, and the linear guide comprises a second magnetic element configured to be magnetically coupled to the first magnetic element.

* * * * *